(12) United States Patent
Kang et al.

(10) Patent No.: US 7,785,864 B2
(45) Date of Patent: Aug. 31, 2010

(54) BIO-MOLECULES DETECTING APPARATUS USING ELECTROMAGNETIC INDUCTION AND DETECTING METHOD USING THE SAME

(75) Inventors: Jung-ho Kang, Suwon-si (KR); Sung-hee Lee, Suwon-si (KR); Young-il Kim, Suwon-si (KR); Moon-chul Lee, Suwon-si (KR); Tae-sik Park, Suwon-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 13 days.

(21) Appl. No.: 11/184,894

(22) Filed: Jul. 20, 2005

(65) Prior Publication Data
US 2006/0019299 A1 Jan. 26, 2006

(30) Foreign Application Priority Data
Jul. 20, 2004 (KR) .................. 10-2004-0056519

(51) Int. Cl.
*C12M 1/34* (2006.01)
*C12M 3/00* (2006.01)
*C12M 1/00* (2006.01)

(52) U.S. Cl. .............. 435/287.2; 435/283.1; 435/6; 422/82.01; 250/306

(58) Field of Classification Search .............. 435/6, 435/283.1, 287.2; 250/306; 422/82.01
See application file for complete search history.

(56) References Cited

U.S. PATENT DOCUMENTS 5,807,758 A * 9/1998 Lee et al. .................. 436/526
7,148,017 B1 * 12/2006 Craighead et al. ............ 435/7.1
7,282,329 B2 * 10/2007 Manalis et al. .............. 435/6

2003/0012693 A1 * 1/2003 Otillar et al. .................. 422/58
2004/0197806 A1 * 10/2004 Yoshida et al. ............... 435/6

(Continued)

FOREIGN PATENT DOCUMENTS

JP 11-160334 A 6/1999

(Continued)

OTHER PUBLICATIONS

Keplinger et al, Lorentz force based magnetic field sensor with optical readout, 2004, Science and Actuators A, 110, 112-118. Published on Feb. 1, 2004.*

Primary Examiner—B J Forman
Assistant Examiner—Narayan K Bhat
(74) Attorney, Agent, or Firm—Sughrue Mion, PLLC

(57) ABSTRACT

Provided are a bio-molecules detecting apparatus using electromagnetic induction and a detecting method using the same. An exemplary apparatus includes: a cantilever of which one end is fixed and the other end is set up to be movable; a first metal formed on a plane of the cantilever and receiving a signal; a bio chip formed in the first metal and having probe biomolecules for searching particular information on a sample to be analyzed; an electromagnetic inductor configured to form a magnetic field; a signal source for applying the signal to the first metal; and a detector for measuring signal values of the first metal before and after the biomolecule is coupled with the sample. The apparatus detects the bio-couple by converting a change in mechanical properties before and after the bio-coupling based on electromagnetic induction to detect a bio-couple.

12 Claims, 5 Drawing Sheets

U.S. PATENT DOCUMENTS

2004/0208788 A1 * 10/2004 Colton .................. 422/68.1

FOREIGN PATENT DOCUMENTS

| JP | 2000-180250 A | 6/2000 |
| JP | 2000-321117 A | 11/2000 |
| JP | 2002-543403 A | 12/2002 |
| WO | 03/083551 A1 | 10/2003 |

* cited by examiner

BIO-MOLECULES DETECTING APPARATUS USING ELECTROMAGNETIC INDUCTION AND DETECTING METHOD USING THE SAME

CROSS-REFERENCE TO RELATED APPLICATIONS

This application claims the benefit of Korean Patent Application No. 2004-56519 filed Jul. 20, 2004, in the Korean Intellectual Property Office, the disclosure of which is incorporated herein by reference.

BACKGROUND OF THE INVENTION

1. Field of the Invention

The present invention relates to a bio-molecules detecting apparatus using electromagnetic induction and a detecting method using the same. More particularly, the present invention relates to a bio-molecules detecting apparatus that detects a bio-couple by using electromagnetic induction and converting changes in mechanical properties before and after the bio-couple into electric signals, and a detecting method using the bio-molecules detecting apparatus.

2. Description of the Related Art

A bio chip is a biological micro chip that can analyze gene expression, gene distribution, and mutation by arraying and immobilizing hundreds to thousands of biomolecules, such as Deoxyribonucleic Acid (DNA), DNA fragments, and Ribonucleic Acid (RNA) whose sequences are known, on a small solid substrate formed of glass, silicon or nylon. On the bio chip, substances, that can serve as a probe for searching particular gene information of a sample, are immobilized. When the bio chip is reacted with a sample to be analyzed, a substance contained in the sample is combined with the probe, immobilized on the surface of the bio chip, thereby forming a state of hybridization. Information on a material contained in the sample can be obtained by detecting and analyzing the hybridization.

Technologies related to the bio chip include technology for attaching and immobilizing a probe, technology for detecting a signal, and technology for processing information. Currently used signal detecting methods are laser-induced fluorescence detection, electrochemical detection, mass detection, and mechanical detection.

FIGS. 1A to 1D are diagrams showing conventional biocouple detecting methods. FIG. 1A is a diagram illustrating a conventional laser-induced fluorescence detection method. The laser-induced fluorescence detection method detects coupling of probe optically by combining a fluorescent substance with a sample and obtaining a result by using a fluorescence detecting device after a coupling reaction between the sample and the probe, and it is widely used at present. However, since the laser-induced fluorescence detection method requires a pre-processing reaction for binding the fluorescence substance with the sample prior to the coupling reaction between the sample and the probe, the sample can be lost or contaminated. Also, after the coupling reaction between the sample and the probe, it needs a complicated optical reader to detect a coupling between the sample and the probe and expensive measuring equipment. In addition, the optical detection method can hardly be miniaturized and it cannot provide a digitalized output.

FIG. 1B shows a conventional mechanical detecting device. The mechanical detection method utilizes a microassembled cantilever to measure a binding force between molecules before and after the coupling between the sample and the probe. However, the mechanical detecting device should be able to measure refraction of a cantilever beam very precisely, and it requires an additional device such as a laser for the precise measurement.

FIGS. 1C and 1D show conventional bio-molecules detecting apparatuses using a capacitor. FIG. 1C illustrates a bio-molecules detecting apparatus using a trench-type capacitor, and FIG. 1D presents bio-molecules detecting apparatus using a plane-type capacitor.

If the bio-molecules detecting apparatus utilizes changes in the characteristics of a capacitor, there is a problem in forming a small-sized capacitor. Since the capacitor is in proportion to a cross-section area and in inverse proportion to a thickness, it is difficult to design the capacitor to perform bio process easily while widening the cross-section area. The bio-molecules detecting apparatus using the trench-type capacitor, which is shown in FIG. 1C, makes the capacitor thin and widens the cross section by forming a deep trench. However, because actual gaps are very small, it is difficult to perform the bio process. FIG. 1D presents a bio-molecules detecting apparatus using a comb-like capacitor on a plane. Since the bio-molecules detecting apparatus has a thin metal film, it has problems that a small number of capacitors are formed and the bio-molecules detecting apparatus has a poor performance in detecting bio-couples.

Another conventional bio-molecules detecting apparatus uses a scanning probe microscope (SPM). The bio-molecules detecting apparatus using an SPM has a problem that it requires additional equipment such as laser equipment and photo diodes.

Another conventional bio-molecules detecting apparatus uses a piezoresistive sensor, which detects bio-couples by detecting pressure, one of basic physical quantities, with the piezoresistive sensor and converting the pressure into electric signals. However, the apparatus has a problem that it is sensitive to the surrounding environment, such as a temperature, and sensitive to procedural errors.

Another conventional bio-molecules detecting apparatus uses a laser diode/photo diode (LD/PD). The apparatus requires many manufacturing processes and high production cost.

SUMMARY OF THE INVENTION

An aspect of the present invention is to provide a bio-molecules detecting apparatus which detects bio-couples by using electromagnetic induction and converting a change in mechanical properties before and after bio coupling into electric signals, and a detecting method using the same.

In accordance with an aspect of the present invention, there is provided an apparatus for detecting a bio-couple by using electromagnetic induction, a cantilever of which one end is fixed and the other end is set up to be movable; a first metal formed on a plane of the cantilever, wherein said first metal receives a signal, having a frequency component, applied thereto; a bio chip formed in the upper part of the first metal, wherein said biochip has a probe biomolecule for searching particular information on a sample to be analyzed; an electromagnetic inductor for forming a magnetic field in a direction perpendicular to—the applied signal direction and on the same plane as the signal applied—to the first metal; a signal source for applying the signal having a frequency component to the first metal; and a detector for measuring signal values of the first metal before and after the probe biomolecule is coupled with the sample, individually.

Herein, the cantilever makes a movement in a direction substantially perpendicular to the plane of the bio chip.

In one non-limiting exemplary embodiment, the electromagnetic inductor is a permanent magnet. In a second non-limiting exemplary embodiment, the electromagnetic inductor is an induced magnet. The detector, in a non-limiting embodiment, can be at least one of an ammeter and a voltmeter.

In another non-limiting exemplary embodiment, the bio-molecules detecting apparatus further includes a second metal which is formed on the cantilever in the lower part of the bio chip separately from the first metal and connected with the detector so that the detector can measure signal values of the second metal before and after the bio-coupling.

Also, the bio-molecules detecting apparatus can be used to detect a chemical gas.

In accordance with another aspect of the present invention, there is provided a method for detecting a bio-couple by using electromagnetic induction, which includes the steps of: a) applying a signal having a frequency component to a first metal formed on a cantilever, of which one end is fixed and the other end is set up to be movable, and forming a magnetic field in a direction perpendicular to a direction in which the signal is applied and in the same plane as the direction the signal, having a frequency component, is applied to the first metal; b) making the cantilever move in a direction substantially perpendicular to the plane of the bio chip, taking as an axis of movement a direction perpendicular to a direction in which the magnetic field is formed, said movement induced by the signal applied to the first metal in conjunction with the presence of the magnetic field, and detecting a signal value of the first metal after the movement of the cantilever; c) bio-coupling a probe biomolecule of the bio chip formed in the upper part of the cantilever with a sample to be analyzed; and d) determining the formation of the bio-couple by detecting the signal value of the first metal after the bio-coupling and comparing the signal value of the first metal after the bio-coupling with the signal value of the first metal before the bio-coupling.

Herein, the signal value of the first metal can be any one of a voltage value of the first metal and a current value of the first metal.

In a non-limiting exemplary embodiment, a second metal is formed in the cantilever formed in a lower part of the bio chip separately from the first metal and the formation of a bio-couple is determined based on a change in a signal value of the second metal by detecting the signal values of the second metal before and after the bio-couple. Herein, the signal value is either a current value of the second metal or a voltage value of the second metal.

Herein, a frequency of movement of the cantilever is changed due to a change in a mass and an elastic coefficient of the cantilever after the bio-coupling.

BRIEF DESCRIPTION OF THE DRAWINGS

The above aspects and features of the present invention will be more apparent by describing certain embodiments of the present invention with reference to the accompanying drawings, in which.

DETAILED DESCRIPTION OF THE EXEMPLARY EMBODIMENTS

Figure 1A:
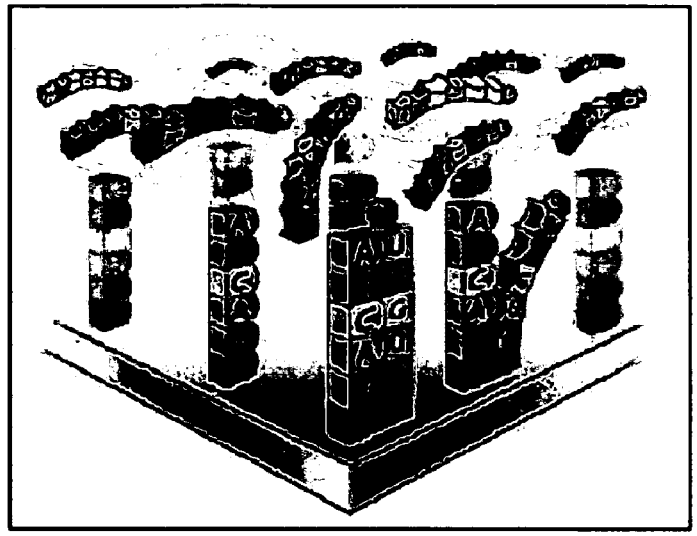
FIGS. 1A to 1D show conventional bio-molecules detecting apparatuses.
Figure 1B:
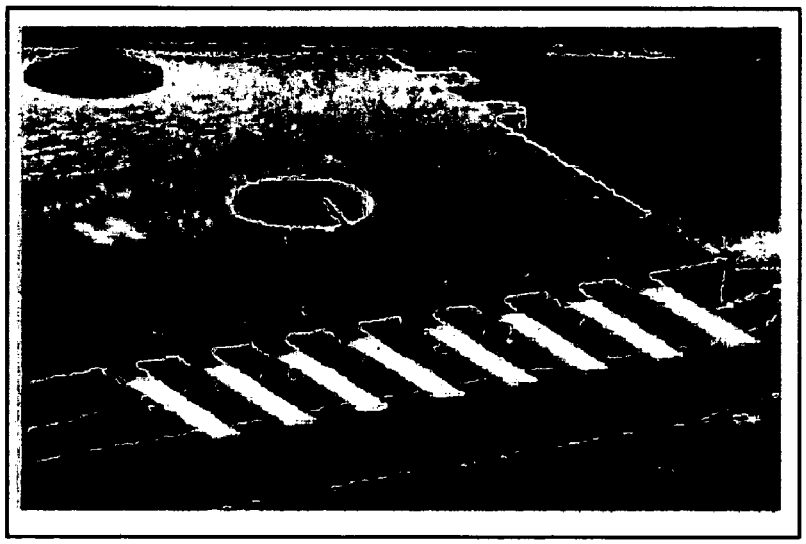
Figure 1C:
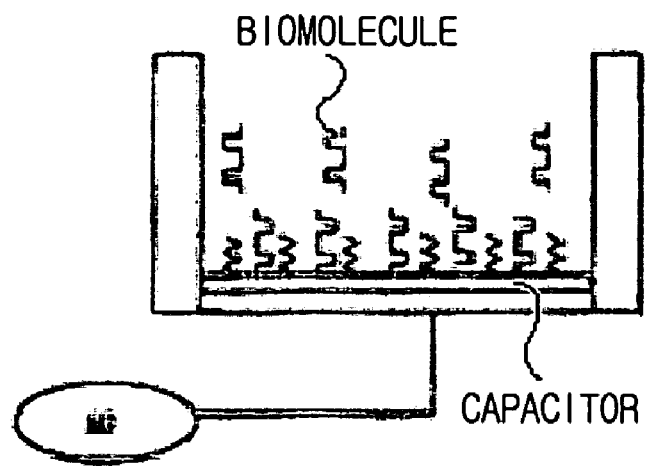
Figure 1D:
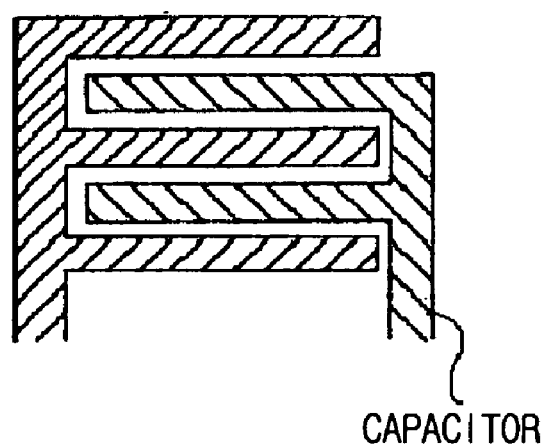

Certain embodiments of the present invention will be described in greater detail with reference to the accompanying drawings.

In the following description, same drawing reference numerals are used for the same elements shown in multiple drawings. The matters defined in the description, such as a detailed construction and elements, are exemplary and non-limiting provided to assist in a comprehensive understanding of the invention. Also, well-known functions or constructions are not described in detail.

Figure 2:
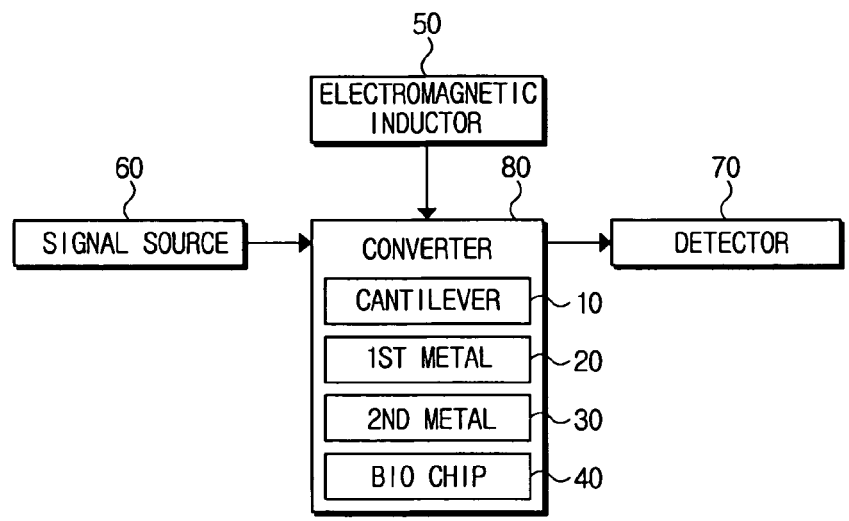
FIG. 2 is a block diagram illustrating a bio-molecules detecting apparatus using electromagnetic induction in accordance with an embodiment of the present invention.

FIG. 2 is a block diagram illustrating a bio-molecules detecting apparatus using electromagnetic induction in accordance with an embodiment of the present invention.

Referring to FIG. 2, the bio-molecules detecting apparatus using electromagnetic induction of the present invention comprises an electromagnetic inductor 50, a signal source 60, a detector 70, and a converter 80. The converter 80 is provided with a cantilever 10, a first metal 20, a second metal 30, and a bio chip 40.

First, the converter 80 includes the first metal 20 and the second metal 30 in the upper part of the cantilever 10. The bio chip 40 is formed in the upper part of the first metal 20 and the second metal 30. The first metal 20 and the second metal 30 are formed in a line shape in the upper part of the cantilever 10 separately. An alternating current is applied to the first metal 20, and an induced current is generated in the second metal 30 due to the movement of the cantilever 10. The bio chip 40 is positioned on the first metal 20 and the second metal 30 formed on the cantilever 10. Probe biomolecules are immobilized to the bio chip 40 to search particular information of a sample to be analyzed.

The electromagnetic inductor 50 generates a magnetic field so that the cantilever 10 makes a movement. The movement direction of the cantilever 10 depends on the direction of the magnetic field formed by the electromagnetic inductor 50. Herein, a permanent magnet or an induced magnet can be used to generate the magnetic field.

The signal source 60 supplies a current having a frequency component by alternating current to the first metal 20.

The detector 70 detects a change in an induced current generated in the second metal 30 before and after a probe biomolecule of the bio chip 40 is coupled with a sample such as Deoxyribonucleic Acid (DNA), Ribonucleic Acid (RNA), protein and biomolecules. However, the second metal 30 may not be formed in some embodiments. In a case where the second metal 30 is not formed, the detector 70 detects a change in a counter electromotive force generated in the first metal 20 before and after the bio-coupling or a change in a current caused by the change in the counter electromotive force. If there is a change in a signal value of the first metal 20 and/or a signal value of the second metal 30, it can be determined that a couple is formed. Herein, the detector 70 can be an ammeter for measuring an electric current or a voltmeter for measuring a voltage.

Figure 3A:
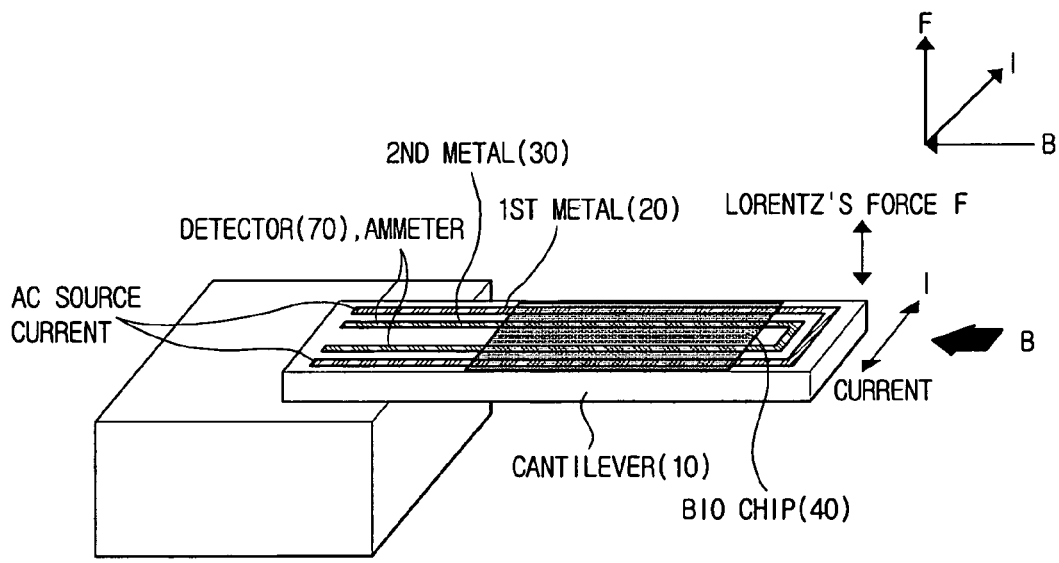
FIG. 3A is a perspective diagram describing a bio-molecules detecting apparatus using electromagnetic induction in accordance with a first embodiment of the present invention.

FIG. 3A is a perspective diagram describing a bio-molecules detecting apparatus using electromagnetic induction in accordance with a first non-limiting embodiment of the present invention. As shown in FIG. 3A, a magnetic field (B) is generated when the signal source 60 supplies alternating current to the first metal 20 formed on the cantilever 10 and an electromagnetic inductor 50, e.g., a permanent magnet, is placed around the first metal 20. When a conductor, through which the electric current flows, such as the first metal 20 is placed in the magnetic field, the Lorentz's Force (F) acts on the conductor, and the cantilever 10 with the first metal 20 formed thereon makes a movement.

If the magnetic field (B) is formed in a direction perpendicular to the alternating current and on the same plane as the alternating current supplied to the first metal 20, the cantilever 10 makes a movement in a direction toward the lower part which is perpendicular to the plane of the bio chip 40 by taking as an axis a direction perpendicular to the direction of the magnetic field according to Fleming's Left Hand Rule, as illustrated in FIG. 3A. If the direction of the alternating current is reversed, the cantilever 10 makes a movement in a direction toward the upper part which is perpendicular to the plane of the bio chip 40 by taking as an axis of movement a direction perpendicular to the direction of the magnetic field. That is, the cantilever 10 makes an up and down movement, substantially perpendicular to the plane of the bio chip 40. taking a direction perpendicular to the direction of the magnetic field as an axis.

Still referring to FIG. 3A, as the cantilever 10 makes a movement in the direction perpendicular to the plane of the bio chip 40, the first metal 20, which is a conductor through which the alternating current flows, is moved to thereby generate a counter electromotive force. Also, an induced current is generated in the second metal 30 by the current of the first metal 20. When the induced current is generated in the second metal 30, the detector 70 (shown as an ammeter) measures a current value or a voltage value of the induced current generated in the second metal 30. The current value or the voltage value measured in the detector 70 is measured before a bio-couple is formed between the sample and the probe biomolecule formed on the bio chip, and the detected value becomes a reference value to be compared with a value detected after bio-coupling.

After the sample is coupled with the probe biomolecule formed on the bio chip 40 and a bio-couple is formed, the mass of the bio chip 40 is increased and the movement of the cantilever 10, i.e., frequency, is changed. In other words, due to the bio-couple, the mass of the bio chip 40 is increased by the mass of the sample and thus the frequency of the movement of the cantilever 10 by the Lorentz's Force (F) is decreased. Since the frequency (w) is in inverse proportion to the square root of the mass (m) and in proportion to the square root of an elastic coefficient (k), $$\left(w \propto \sqrt{\frac{k}{m}}\right),$$

the frequency of the movement of the cantilever 10 is decreased. Since the bio couple changes the frequency of the movement of the cantilever 10, the induced current value or the voltage value of the second metal 30 is changed. This way, the presence of the bio-couple can be detected.

Meanwhile, as the sample is coupled with the probe biomolecule, that is, as the bio-couple is formed, tension of the surface of the bio chip 40 is changed and thus mechanical properties are changed. As a result, the elastic coefficient (k) of the movement of the cantilever 10 is changed. In other words, since the frequency is in proportion to the square root of the elastic coefficient, the frequency of the movement of the cantilever 10 is changed due to the bio-couple, and the induced current value of the second metal 30 or the voltage value of the second metal 30 detected in the detector 70 is changed. Therefore, the formation of the bio-couple can be detected by measuring the change in the current value or the voltage value detected in the detector 70.

Figure 3B:
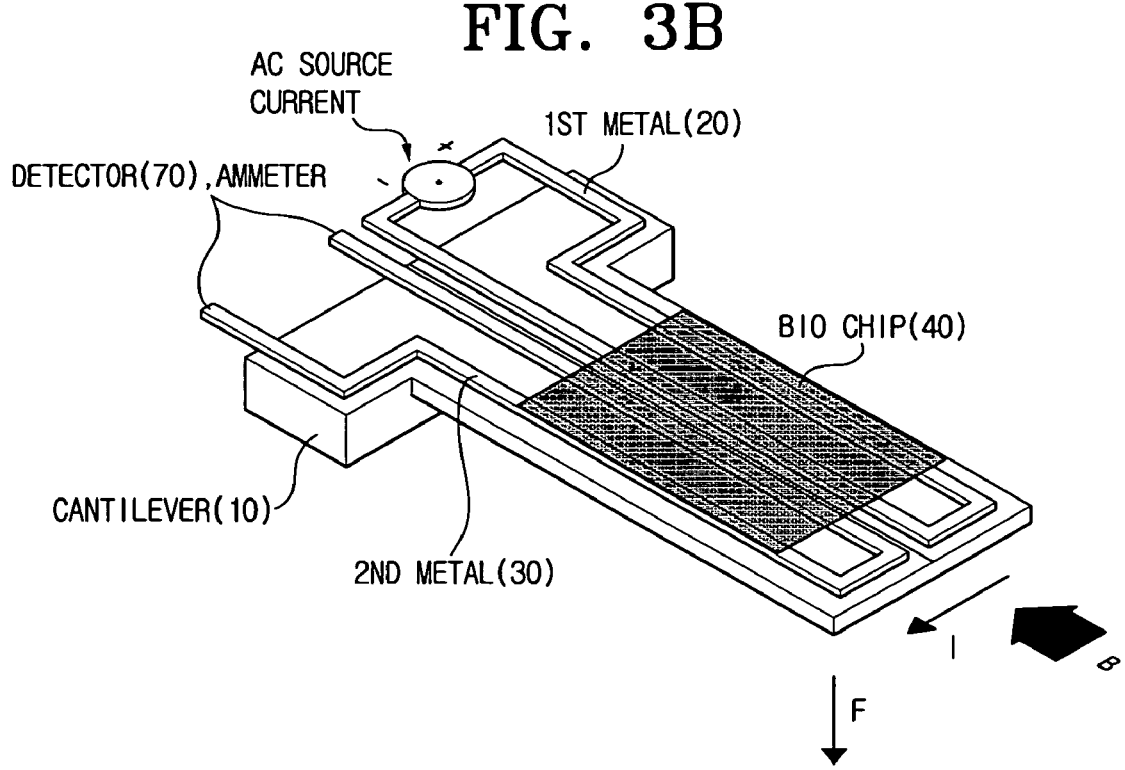
FIG. 3B is a perspective diagram describing a bio-molecules detecting apparatus using electromagnetic induction in accordance with a second embodiment of the present invention.

FIG. 3B is a perspective diagram describing a bio-molecules detecting apparatus using electromagnetic induction in accordance with a second non-limiting embodiment of the present invention. Referring to FIG. 3B, the cantilever 10 is operated and the formation of the bio-couple can be detected in the same principle as the case of FIG. 3A, although the shapes of the first metal 20 and the second metal 30 are different from those of FIG. 3A.

Figure 3C:
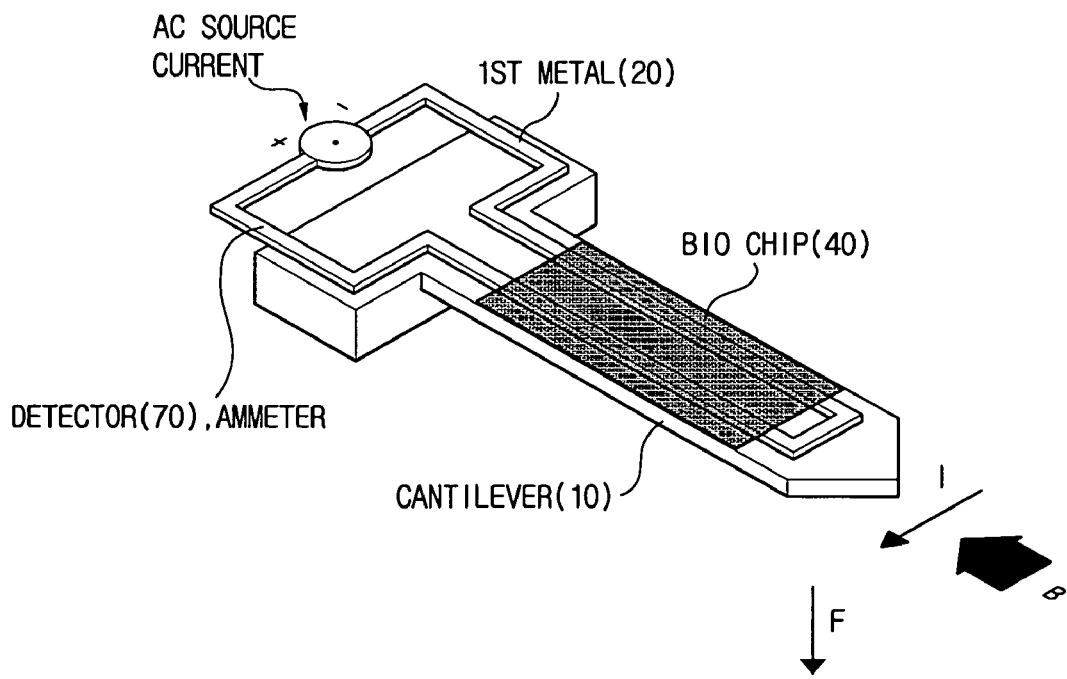
FIG. 3C is a perspective diagram describing a bio-molecules detecting apparatus using electromagnetic induction in accordance with a third embodiment of the present invention.

FIG. 3C is a perspective diagram describing a bio-molecules detecting apparatus using electromagnetic induction in accordance with a third non-limiting embodiment of the present invention. The bio-molecules detecting apparatus of FIG. 3C based on electromagnetic induction includes only the first metal 20 without the second metal 30, which is different from non-limiting embodiments shown in FIGS. 3A and 3B. Therefore, the detector 70 (shown as an ammeter) measures the changed current value or voltage value of the first metal 20, instead of measuring the changed current value or voltage value of the second metal 30 before and after the bio-coupling.

In FIG. 3C, when alternating current is applied to the first metal 20, before bio coupling, and when the magnetic field is formed in a direction perpendicular to the current direction and on the same plane as the plane in which the alternating current flows, the cantilever 10 makes a movement by the Lorentz's Force (F) as shown in FIG. 3C, which is also described with reference to FIGS. 3A and 3B. In short, the cantilever 10 makes a movement in a direction perpendicular to the plane of the bio chip 40 by taking a direction perpendicular to the direction of the magnetic field as an axis. As a result, a counter electromotive force is generated in the first metal 20 and the current that flows through the first metal 20 is reduced by the counter electromotive force. A measured current value before the bio-coupling becomes a reference to be compared with a current value after the bio-coupling.

After the bio-coupling, the mass of the bio chip 40 formed in the upper part of the cantilever 10 is increased corresponding to the mass of the sample coupled with the probe biomolecule of the bio chip 40. Thus, the mass of the cantilever 10 is increased and the frequency of the movement of the cantilever 10 is decreased. Since the counter electromotive force is in proportion to the frequency, the decrease in the frequency leads to a decrease in the counter electromotive force generated in the first metal 20. Due to the decreased counter electromotive force, the entire voltage applied to the first metal 20 is increased and, thus, the value of the current that flows through the first metal 20 is increased.

For example, when the current (I) applied to the first metal 20 from the signal source 60 is Asinwt (I=Asinwt) and the magnetic field (B) is formed, the Lorentz's force (F) that acts on the cantilever 10 is BLAsinwt (F=BLAsinwt). Herein, L is the length of the conductive wire on which the Lorentz's force acts, and w is angular frequency. When the current that flows through the first metal 20 by the generation of the counter electromotive force (e) before bio-coupling is I' and the current that flows through the first metal 20 by the reduced counter electromotive force (e') after the bio-coupling is I", the current I' that flows through the first metal 20 before the bio-couple is (V−e)/R (I'=(V−e)/R). And the current I" that flows through the first metal 20 by the decreased counter electromotive force (e') after the bio-couple is (V−e')/R (I"= (V−e')/R). Herein, V denotes a voltage applied to the first metal 20 by the signal source 60; e denotes a counter electromotive force before bio-coupling; and e' denotes a counter electromotive force after bio-coupling. As e' has a smaller value than e, I" has a larger value than I'. Therefore, the formation of the bio-couple can be detected by detecting the current I" that flows through the first metal 20 after the bio-couple has a value larger than the current I' that flows through the first metal 20 before the bio-coupling detected with an ammeter.

Figure 3D:
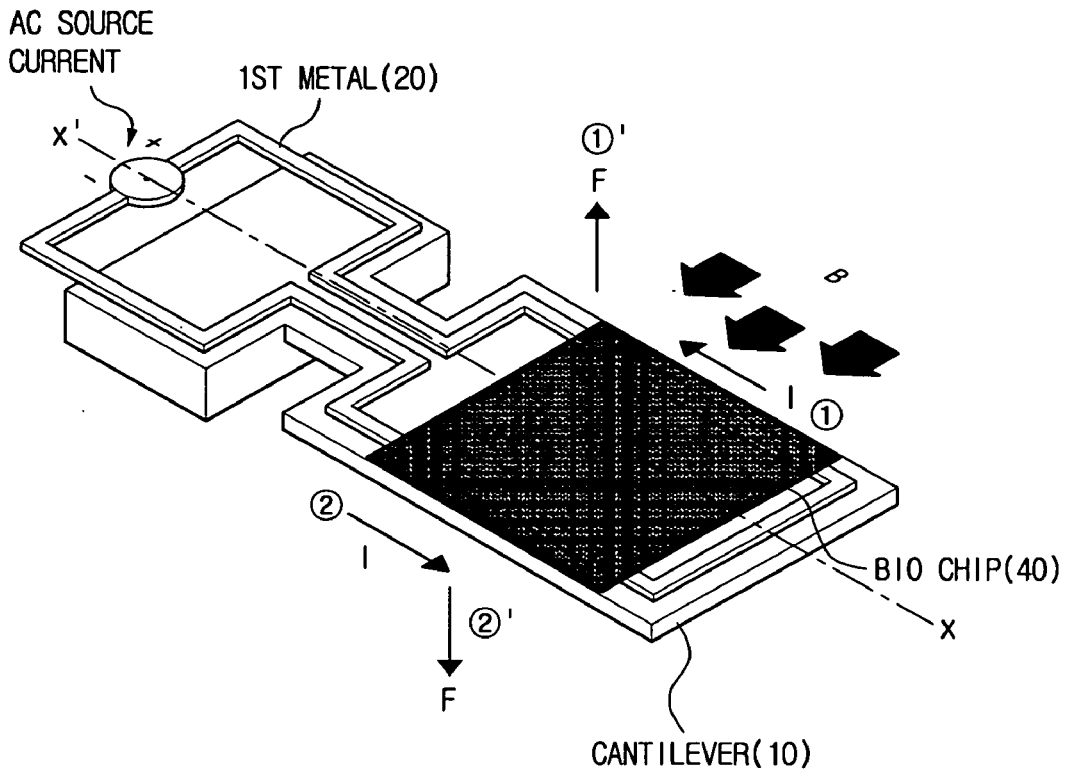
FIG. 3D is a perspective diagram describing a bio-molecules detecting apparatus using electromagnetic induction in accordance with a fourth embodiment of the present invention.

FIG. 3D is a perspective diagram describing a bio-molecules detecting apparatus before electromagnetic induction in accordance with a fourth non-limiting embodiment of the present invention. In FIG. 3D, the magnetic field is formed in a direction different from the direction where the magnetic field is formed in FIG. 3C. Since FIG. 3D is different from FIG. 3C in the direction where the magnetic field is formed, the operation principle is analogous to the operation corresponding to FIG. 3C, except that the direction that the cantilever 10 moves is different.

Referring to FIG. 3D, the cantilever 10 makes a movement in a direction substantially perpendicular to the plane of the bio chip 40. Referring to FIG. 3D, the magnetic field is formed as shown and the applied current flows counter clockwise through the first metal 20 in a side ① and in a side ②, the direction of the applied current, I, is indicated by arrows. When the current flows in side ①, the Lorentz's Force F acts in a direction ①'. On the other hand, if the current flows through the first metal 20 in the side ②, then, the Lorentz's Force F acts in a direction ②'. Therefore, the cantilever 10 makes a frequency movement in the directions ①' and ②' based on an axis x-x'.

Referring to FIGS. 3C and 3D, the cantilever 10 makes a movement in a different direction by making the direction of the magnetic field different in the bio-molecules detecting apparatus that uses electromagnetic induction and includes only the first metal 20. However, it is possible to make the movement direction of the cantilever 10 different by forming the magnetic field direction as shown in FIG. 3D in various bio-molecules detecting apparatus embodiments of FIGS. 3A, 3B and 3C that use electromagnetic induction and include the first metal 20 and the second metal 30. The operation principle is the same as described in FIG. 3D.

Figure 4:
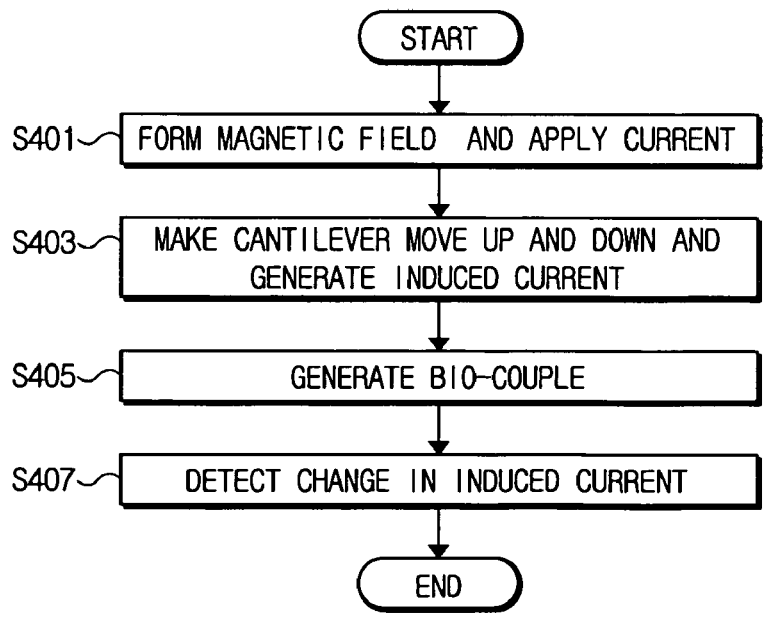
FIG. 4 is a flowchart depicting a bio-couple detecting method using electromagnetic induction in accordance with an embodiment of the present invention.

FIG. 4 is a flowchart depicting a bio-couple detecting method using electromagnetic induction in accordance with an embodiment of the present invention. Referring to FIG. 4, at step S401, alternating current is applied to the first metal 20 formed on the cantilever 10 from the signal source 60, and a magnetic field is formed around the cantilever 10 by a permanent magnet or an induced magnet provided by the electromagnetic inductor 50 in the various bio-molecules detecting apparatus embodiments, using electromagnetic induction.

Bio-coupling can be detected by the bio-couple detecting method as shown in FIG. 2 and FIGS. 3A to 3D, and furthermore, generation of certain chemical gas can also be detected according to the above-described principle.

Referring to FIG. 4 and FIGS. 3A and 3B, when an electric alternating current flows through the first metal 20 and the magnetic field is formed, at step S403, the cantilever 10 makes a movement by the Lorentz's Force to thereby generate a counter electromotive force in the first metal 20 and generate an induced current in the second metal 30. If the magnetic field is formed in a direction perpendicular to the direction of the current on the same plane as the direction of the current that flows through the first metal 20 of the cantilever 10, the cantilever 10 moves in a direction perpendicular to the plane of the bio chip 40 by taking the direction perpendicular to the direction of the magnetic field as an axis. That is, the cantilever 10 makes an up and down movement. As the cantilever 10 makes the up and down movement, the corresponding change in direction upon which the magnetic field acts upon the first metal, generates a counter electromotive force in the first metal 20 and generates an induced current in the second metal 30.

The detector 70 detects the induced current generated in the second metal 30. The detector 70 can be an ammeter for measuring an electric current or a voltmeter for measuring a voltage. The induced current value measured in the detector 70 is an induced current value before the bio-coupling, that is, before a probe biomolecule formed in the bio chip 40 is coupled with the sample. The induced current value measured in the detector 70 becomes a reference to be compared with an induced current value after the bio-coupling. Herein, the bio-molecules detecting apparatus using electromagnetic induction may not include the second metal 30. If the apparatus does not include the second metal 30 (as shown in FIGS. 3C and 3D), the formation of the bio-couple can be detected by measuring a voltage value or a current value changed by the counter electromotive force generated in the first metal 20.

Subsequently, at step S405, the induced current generated in the second metal 30 is detected after the probe molecule formed in the bio chip 40 is coupled with the sample, e.g., DNA, RNA, protein and the like. If there is a bio-couple, the mass of the bio chip 40 is increased or the elastic coefficient of the cantilever 10 that makes a frequency movement is changed, which is described above with reference to FIGS. 3A and 3B. As the mass of the cantilever 10 is changed or the frequency movement of the cantilever 10 is changed due to the change in the elastic coefficient, the induced current value generated in the second metal 30 is changed, too. The changed induced current value is detected in the detector 70.

However, if the second metal 30 is not formed, the detector 70 detects a change in the voltage value or current value of the first metal 20, which is caused by the change in the counter electromotive force generated in the first metal 20.

At step S407, the induced current values generated in the second metal 30 before and after the bio-coupling are compared. If there is not the second metal 30, the voltage values or the current values of the first metal 20 before and after the bio-coupling are compared. If there is a change in the voltage values or the current values of the first metal 20 before and after the bio-coupling, it is determined that a bio-couple is formed.

As described above, the technology of the present invention can improve the performance of bio-couple detection and shorten the time for detecting a bio-couple by using electromagnetic induction and converting a change in mechanical properties before and after bio-coupling into electric signals to detect the bio-couple.

The bio-molecules detecting apparatus of the present invention detects the bio-couple only based on a change in electric signals.

The foregoing embodiment and advantages are merely exemplary and are not to be construed as limiting the present invention. The present teaching can be readily applied to other types of apparatuses. Also, the description of the embodiments of the present invention is intended to be illustrative, and not to limit the scope of the claims, and many alternatives, modifications, and variations will be apparent to those skilled in the art.

What is claimed is:

1. An apparatus for detecting bio-molecules by using electromagnetic induction, comprising:
   a cantilever of which one end is fixed and another end is set up to be movable;
   a first metal formed in a line shape in an upper plane of the cantilever, said first metal receiving a current signal, having a frequency component, applied thereto;
   a bio chip formed of a solid substrate of one of glass, silicon and nylon, wherein the bio chip is positioned on an upper part of the first metal, wherein the bio chip has a probe biomolecule for searching particular information on a sample to be analyzed, and wherein a lower surface of the bio chip abuts an upper surface of the first metal;
   a magnetic field source configured to form a magnetic field in a direction perpendicular to a direction the signal is applied, said magnetic field being on the same plane as the direction of the signal applied to the first metal;
   a signal source configured to apply the current signal having a frequency component to the first metal so that the cantilever makes an up and down movement;
   a detector configured to measure current signal values of the first metal before and after the probe biomolecule is bio-coupled with the sample, individually, wherein the current signal values of the first metal is determined based on the movement of the cantilever; and
   a second metal which is in a line shape and formed on the cantilever in the lower part of the bio chip separately from the first metal, and connected with the detector so that the detector can measure induced current signal values of the second metal before and after bio-coupling, wherein the first and second metals are separated by a portion of the cantilever, and wherein the induced current signal is induced in the second metal by the movement of the cantilever.

2. The apparatus as recited in claim 1, wherein the cantilever makes a movement in a direction substantially perpendicular to the plane of the bio chip.

3. The apparatus as recited in claim 1, wherein the magnetic field source comprises a permanent magnet.

4. The apparatus as recited in claim 1, wherein the magnetic field source comprises an induced magnet.

5. The apparatus as recited in claim 1, wherein the detector comprises at least one of an ammeter and a voltmeter.

6. The apparatus as recited in claim 1, wherein a frequency of movement of the cantilever, after the probe biomolecule is bio-coupled with the sample, is changed as compared to a frequency of movement of the cantilever before the probe biomolecule is bio-coupled with the sample.

7. The apparatus as recited in claim 1, wherein the signal received by said first metal is an electrical signal.

8. The apparatus as recited in claim 7, wherein the electrical signal is an alternating current.

9. The apparatus as recited in claim 1, wherein the bio chip comprises a biological micro chip which analyzes at least one of gene expression, gene distribution and mutation by arraying and immobilizing biomolecules.

10. The apparatus as recited in claim 1, wherein the first metal extends in a straight line in conformity with a substantial portion of the perimeter of the cantilever.

11. The apparatus as recited in claim 1, wherein both the first metal and second metals extend in a straight line in conformity with a portion of the perimeter of the cantilever.

12. The apparatus as recited in claim 1, wherein both the first metal and second metals are in a same upper plane of the cantilever.

\* \* \* \* \*